US009398363B2

(12) United States Patent
Takeno et al.

(10) Patent No.: US 9,398,363 B2
(45) Date of Patent: Jul. 19, 2016

(54) NECKBAND-TYPE EARPHONE

(71) Applicant: D&M Holdings, Inc., Kanagawa (JP)

(72) Inventors: Katsuyoshi Takeno, Kanagawa (JP); Yoshinari Fukushima, Kanagawa (JP)

(73) Assignee: D&M Holdings, Inc., Kanagawa (JP)

( * ) Notice: Subject to any disclaimer, the term of this patent is extended or adjusted under 35 U.S.C. 154(b) by 0 days.

(21) Appl. No.: 14/367,560

(22) PCT Filed: Dec. 12, 2012

(86) PCT No.: PCT/JP2012/082161
§ 371 (c)(1),
(2) Date: Jun. 20, 2014

(87) PCT Pub. No.: WO2013/094484
PCT Pub. Date: Jun. 27, 2013

(65) Prior Publication Data

US 2015/0172802 A1 Jun. 18, 2015

(30) Foreign Application Priority Data

Dec. 22, 2011 (JP) ................................ 2011-281899
Dec. 27, 2011 (JP) ................................ 2011-285729

(51) Int. Cl.
*H04R 5/02* (2006.01)
*H04R 1/10* (2006.01)
(Continued)

(52) U.S. Cl.
CPC ................ *H04R 1/105* (2013.01); *H04R 5/033* (2013.01); *H04R 5/0335* (2013.01); *H04R 1/005* (2013.01); *H04R 1/1008* (2013.01);
(Continued)

(58) Field of Classification Search
USPC ................................................. 381/309, 330
See application file for complete search history.

(56) References Cited

U.S. PATENT DOCUMENTS 5,459,290 A 10/1995 Yamagishi
6,233,345 B1 5/2001 Urwyler
(Continued)

FOREIGN PATENT DOCUMENTS

EP 0779763 6/1997
EP 2053874 A1 4/2009
(Continued)

OTHER PUBLICATIONS

European Search Report issued on EP 12859150.0, dated Jul. 8, 2015.

*Primary Examiner* — Amir Etesam
(74) *Attorney, Agent, or Firm* — Peter A. Nieves; Sheehan Phinney Bass & Green PA

(57) ABSTRACT

[Problem] The purpose of the present invention is to provide a neckband-type earphone that can be worn for a long time without subjecting the wearer to discomfort of wearing a neckband-type earphone, and in which the extent of hazard to the wearer when worn is lowered and locations that break are reduced. [Solution] A neckband-type earphone provided with: earphone parts which are inserted into the pinnae of the wearer and which output an audio signal; ear holder parts which connect to the earphone parts and which abut the upper side of the pinnae of the wearer; holder bodies provided with the ear holder parts; earphone drivers provided with the holder bodies; and a neck band connecting the two earphone drivers; the holder bodies being provided with a cushion part at a portion that comes into contact with the head of the wearer in the vicinity of the pinnae.

7 Claims, 7 Drawing Sheets

(51) Int. Cl.
*H04R 5/033* (2006.01)
*H04R 1/00* (2006.01)

(52) U.S. Cl.
CPC ............ *H04R 1/1016* (2013.01); *H04R 1/1041* (2013.01); *H04R 2460/17* (2013.01)

(56) References Cited

U.S. PATENT DOCUMENTS

| | | | | |
|---|---|---|---|---|
| 7,209,177 | B2 * | 4/2007 | Lapalme | B21F 1/002 348/375 |
| 8,009,853 | B2 * | 8/2011 | Ito | H04R 1/1066 381/370 |
| 2007/0003093 | A1 | 1/2007 | Ito et al. | |
| 2008/0260197 | A1 | 10/2008 | Polito | |
| 2011/0088699 | A1 * | 4/2011 | Skipper | A61M 16/06 128/206.26 |

FOREIGN PATENT DOCUMENTS

| | | | |
|---|---|---|---|
| GB | 1091490 | | 11/1967 |
| JP | 6-81193 | U | 11/1994 |
| JP | 2002238092 | A | 8/2002 |
| JP | 2008-161429 | A | 7/2006 |
| JP | 2007-013873 | A | 1/2007 |
| JP | 2008-227754 | A | 9/2008 |
| JP | 2010-268030 | A | 11/2010 |
| WO | 2010-116510 | A1 | 10/2010 |

* cited by examiner

NECKBAND-TYPE EARPHONE

TECHNICAL FIELD

The present invention relates to a neckband-type earphone.

BACKGROUND ART

In recent years, as an earphone for a portable audio reproducing device, an inner-ear-type earphone, a neckband-type earphone, and the like have been becoming widely used. Of the above-mentioned earphones, the neckband-type earphone includes relatively small headphones and is excellent in design unlike a headphone device in which a band section for coupling driver units together is held over a head.

In the neckband-type earphone, driver units of earphones are coupled by a band section. The band section has a U-shape, and a band of the band section is arranged in a vicinity of a back of a head of a wearer when the wearer wears the neckband-type earphone. The neckband-type earphone as described above is disclosed (for example, see Patent Literatures 1 and 2).

Further, as another related-art earphone, there is known a neckband-type earphone in which a reproducing unit for reproducing an audio signal is provided on a back side of a neckband (for example, see Patent Literature 3). In such a related-art neckband-type earphone, the reproducing unit itself is provided in the neckband-type earphone, and hence it is not necessary to connect the reproducing device and the neckband-type earphone through a cable. Accordingly, for example, when a user walks during commuting to work or plays sports such as jogging, the user does not need to care about the cable and can concentrate on playing sports.

Further, in recent years, a device for transmitting the audio signal through a radio wave has been known as means for transmitting the audio signal from the reproducing device to the earphone, instead of transmitting the audio signal from the reproducing device to the earphone through the cable as in the related art. In a case of the above-mentioned device for transmitting the audio signal through the radio wave, the reproducing device includes a transmitting unit for outputting the audio signal through the radio wave, whereas the earphone includes a receiving unit for receiving the audio signal. Thus, through the radio wave, the neckband-type earphone receives the audio signal reproduced by the reproducing device.

CITATION LIST

Patent Literature

[PTL 1] JP 2007-013873 A
[PTL 2] JP 2008-227754 A
[PTL 3] JP 2002-238092 A

SUMMARY OF INVENTION

Technical Problems

In the headphone device disclosed in Patent Literature 1, two headphone housings for right and left ears are provided to a U-shaped band section. A driver unit is built in each of the two headphone housings. Each distal end portion of the band section is held on a temple of the wearer in a vicinity of an upper end of a right or left auricle, and an intermediate portion of the band section is arranged on a back of a head of the wearer. The distal end portion of the band section protrudes forward with respect to the auricle of the wearer, and a vicinity of the distal end portion of the band section is brought into abutment on the head of the wearer. In this manner, the entire headphone device is securely attached on the head of the wearer.

However, in the headphone device, the vicinity of the distal end portion of the band section, tightens the head of the wearer. This may bring the wearer a headache when the wearer wears the headphone device for a long period of time. The vicinity of the distal end of the band section of the headphone device is brought into abutment on a vicinity of the temple of the head. Further, in order to securely attach the headphone device on the head, an elastic material is used for the band, section, and the band section is formed so that the distal end portion of the band section is securely brought into abutment on the head due to elasticity of the elastic material. Therefore, when the headphone device is attached on the head of the wearer, the band section tightens the head, and hence the headphone device is not suitable for wearing for a long period of time.

Further, the band section and the headphone housings of the headphone device come into contact with the head of the wearer, and thus the headphone device is held on the head. However, a portion of the headphone device abutting on the head comes into not surface-contact but line-contact with the head of the wearer. This causes the wearer to feel a sense of instability, and the wearer cannot feel a sense of stability when wearing the headphone device.

Further, the headphone device includes protruding distal ends of the band section, and hence there is a risk in that the distal ends of the band section may hit the ear or the back of the head of the wearer by mistake when the wearer uses the headphone device. The neckband-type headphone device is becoming widely used, but some people do not yet know how to use the neckband-type headphone device. The headphone device including the distal end portions has a special shape as a headphone device. Accordingly, when the wearer uses a portable device outdoors and also puts on the headphone device at night, the wearer may forget that the headphone device includes the distal end portions, and hence there is a risk in that the distal end portions may hit the ear or the head of the wearer when the wearer puts on the headphone device.

In addition, the headphone device has such a shape that the headphone housings are provided to the band section including the distal end portions. Thus, the headphone device is reduced in strength as a whole, and hence the distal end portions may be broken and damaged.

The neckband-type earphone that receives, through the radio wave, the audio signal reproduced by the reproducing device needs to include a control unit for controlling volume of the audio signal and the like, a battery for supplying power, and the like in addition to the receiving unit for receiving the radio wave from the reproducing device. Accordingly, in a case where the neckband-type earphone as disclosed in Patent Literature 2 receives the audio signal from the reproducing device through the radio wave, the receiving unit, the control unit, and the battery described above need to be provided in each housing, and hence a weight of the housing is increased. In a case where the weight of the housing is increased as described above, for example, when the user walks during commuting to work or while the user plays sports such as jogging, the neckband-type earphone may fall off or slip off the ear due to the weight of the housing.

Further, in the neckband-type earphone as disclosed in Patent Literature 3 in which the reproducing unit is provided on a back portion of a neckband, the control unit, the battery, and the like can be provided in the reproducing unit. However, when the user walks during commuting to work or plays sports such as jogging under a state in which the reproducing unit is held on the back of the head, a load of a weight of the reproducing unit provided on the back portion of the neckband is transmitted to the head of the user every time the head of the user vibrates. As a result, the head is tilted backward due to the weight of the reproducing unit, which may significantly deteriorate wearing comfort of the neckband-type earphone.

Therefore, it is an object of the present invention to provide a neckband-type earphone that enables a wearer to wear the neckband-type earphone for a long period of time without giving discomfort of wearing to the wearer, reduces a risk to the wearer when the wearer puts on the neckband-type earphone, also reduces a damage-prone portion, and is capable of preventing slip of the neckband-type earphone off the ear and deterioration of wearing comfort even when the user commutes to work or plays sports in a state of wearing the neckband-type earphone.

Solution to Problems

According to one embodiment, of the present invention, there is provided a neckband-type earphone, including; an earphone section to be inserted into an auricle of a wearer, for outputting an audio signal; an ear holder section connected to the earphone section and to be brought into abutment on an upper side of the auricle of the wearer; a holder body including the ear holder section; earphone drivers each including the holder body; and a neckband for connecting two of the earphone drivers together, in which the holder body includes a cushion section on a portion that comes into contact with a head of the wearer in a vicinity of the auricle.

Further, in the above-mentioned, neckband-type earphone according to one embodiment of the present invention, the cushion, section includes a plurality of convex portions.

Further, in the above-mentioned neckband-type earphone according to one embodiment of the present invention, each of the plurality of convex portions of the cushion section has a hollow formed therein, or an inside of each of the plurality of convex portions of the cushion section has a charging material injected thereto.

Further, in the above-mentioned neckband-type earphone according to one embodiment of the present invention, each of the plurality of convex portions of the cushion section has a circular shape or a polygonal shape.

Further, in the above-mentioned neckband-type earphone according to one embodiment of the present invention, the plurality of convex portions of the cushion section include a circular convex portion and a polygonal convex portion in a mixed manner.

Further, according to another embodiment of the present invention, there is provided a neckband-type earphone for outputting an audio signal, including: a neckband section formed of an elastic body into a curved shape; a driver unit fixed to a housing, the driver unit including a diaphragm for emitting the audio signal as sound; a head holding section connected to the neckband section, for outputting the audio signal to the driver unit; and an arm section formed of a curved elastic body, for connecting the head holding section and the housing together, in which the head holding section includes a plurality of dimple portions for forming recesses in a side surface of the head holding section.

Further, in the above-mentioned neckband-type earphone according to another embodiment of the present invention, each of the plurality of dimple portions is formed of an elastic body.

Further, in the above-mentioned neckband-type earphone according to another embodiment, of the present invention, the head holding section includes: as audio signal receiving unit for receiving the audio signal; and an audio signal outputting unit, for outputting, to the driver unit, the audio signal received by the audio signal receiving unit.

Advantageous Effects of Invention

According to one embodiment of the present invention, it is possible to provide the neckband-type earphone that enables the wearer to wear the neckband-type earphone for a long period of time without giving discomfort of wearing to the wearer, reduces the risk to the wearer when the wearer puts on the neckband-type earphone, also reduces the damage-prone portion, and is capable of preventing slip of the neckband-type earphone off the ear and deterioration of the wearing comfort even when the user commutes to work or plays sports in a state of wearing the neckband-type earphone.

DESCRIPTION OF EMBODIMENTS (First Embodiment)

Now, a first embodiment of the present invention is described with reference to the drawings.

Figure 1A:
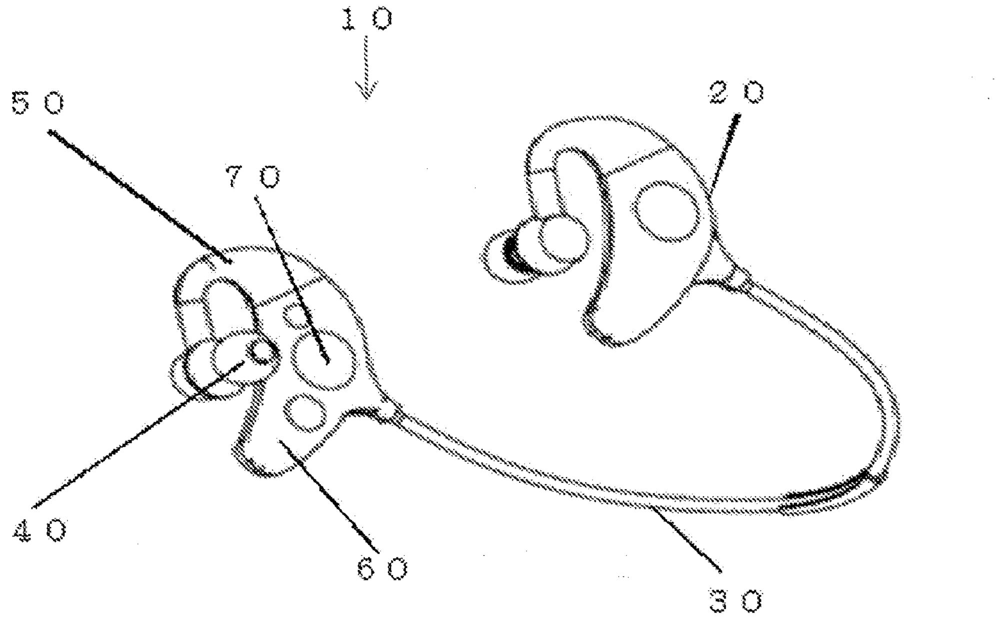
FIG. 1 are views illustrating a schematic configuration of a neckband-type earphone according to a first embodiment of the present invention.
Figure 1B:
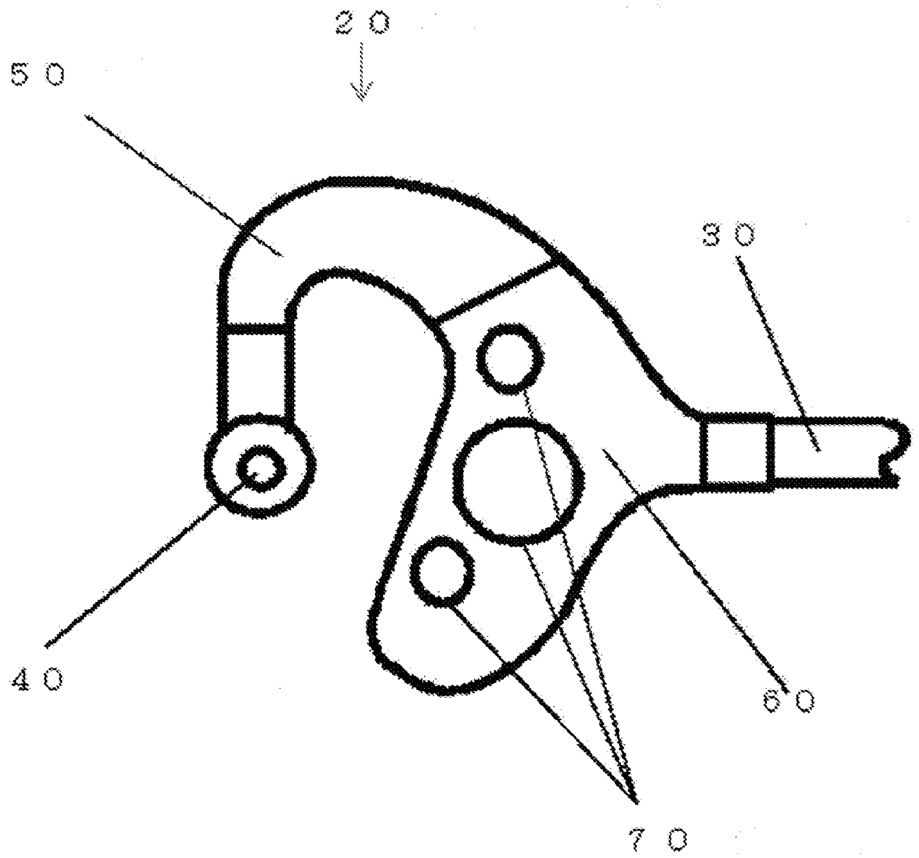

FIG. 1 ere views illustrating a schematic configuration of a neckband-type earphone according to a first embodiment of the present invention. FIG. 1(*a*) is a view illustrating an entire schematic configuration of the neckband-type earphone. FIG. 1(*b*) is a view illustrating a schematic configuration of an earphone driver of the neckband-type earphone.

In FIG. 1(*a*), a neckband-type earphone 10 includes two earphone drivers 20 and a neckband 30. The neckband 30 has a U-shape, and the earphone drivers 20 are respectively provided to two end portions of the neckband 30. Note that, both ends of the U-shape of the neckband 30 are slightly curved inward. The two earphone drivers 20 are arranged on auricles of a wearer, and the neckband 30 is arranged on a back side of a neck of the wearer. In this manner, the neckband-type earphone 10 is attached on the wearer.

In FIG. 1(*b*), each of the earphone drivers 20 includes an earphone section 40, an ear holder section 50, and a holder body 60. The earphone section 40 is inserted into the auricle of the wearer so as to output an audio signal. The ear holder section 50 connects the earphone section 40 to the holder body 60 described below. The ear holder section 50 comes into contact with an upper side of the auricle of the wearer so as to hold the neckband-type earphone 10. The holder body 60 includes a built-in driver (not shown) for converting an electric signal into the audio signal, and holds the earphone section 40 through intermediation of the ear holder section 50. Further, the holder body 60 includes a cushion section 70 that comes into contact with a head of the wearer in a vicinity of the auricle.

In the neckband-type earphone 10, the ear holder section 50 of each earphone driver 20 comes into contact with the upper side of the auricle of the wearer, and the holder body 60 comes into contact with the head of the wearer in a vicinity of a back of the auricle. Both ends of the U-shaped neckband 30 are curved inward. Thus, the neckband-type earphone 10 is held on the head of the wearer.

Figure 2A:
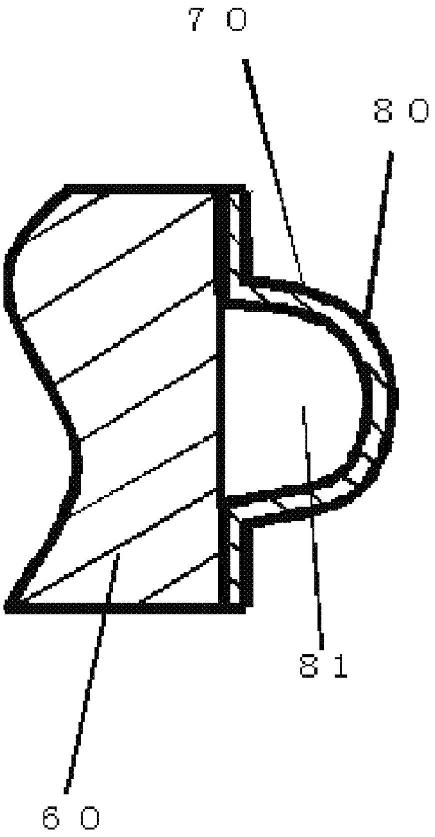
FIG. 2 are views illustrating structure of a cushion section of the neckband-type earphone according to the first embodiment of the present invention.
Figure 2B:
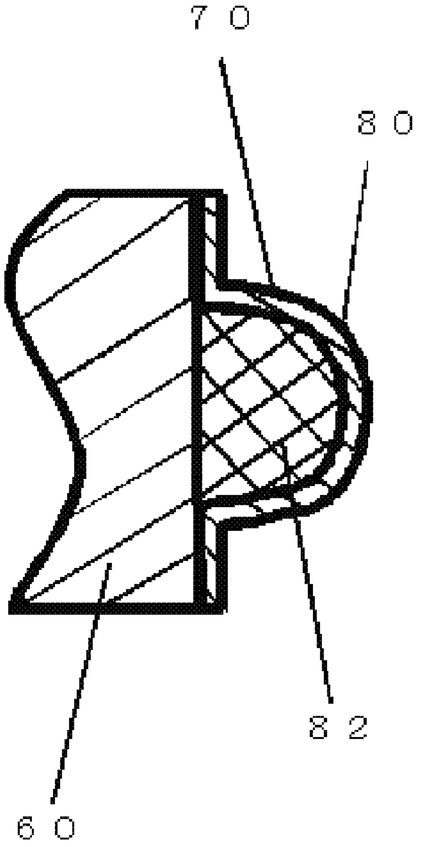
Figure 3A:
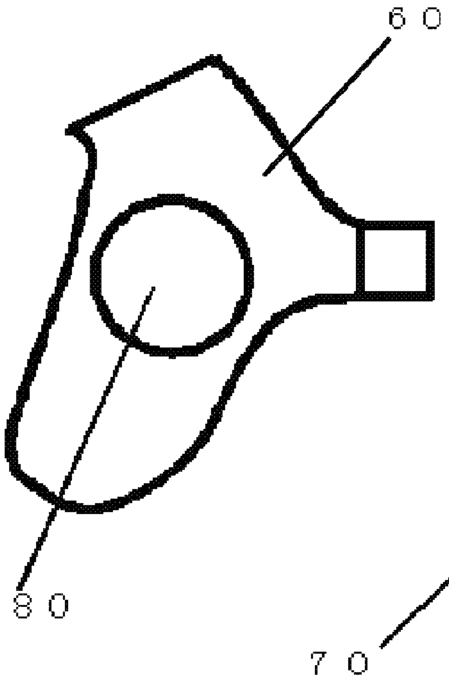
FIG. 3 are views illustrating the cushion section of the neckband-type earphone according to the first embodiment of the present invention.
Figure 3B:
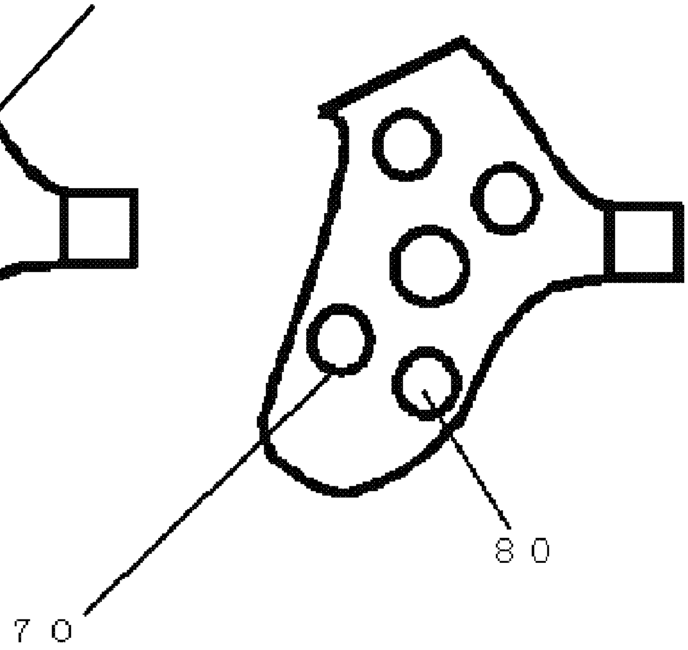
Figure 3C:
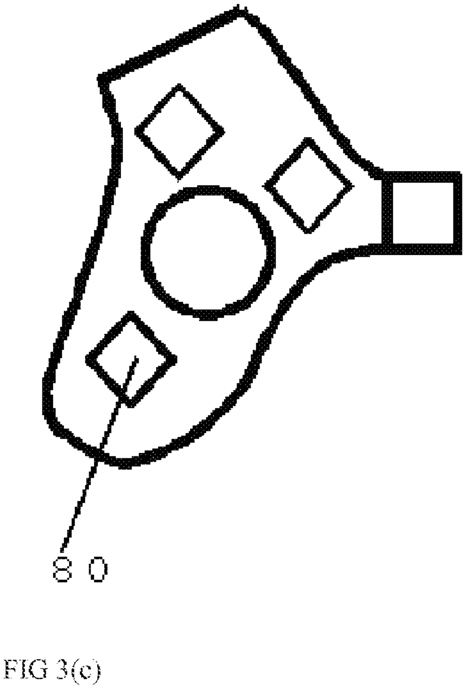
Figure 3D:
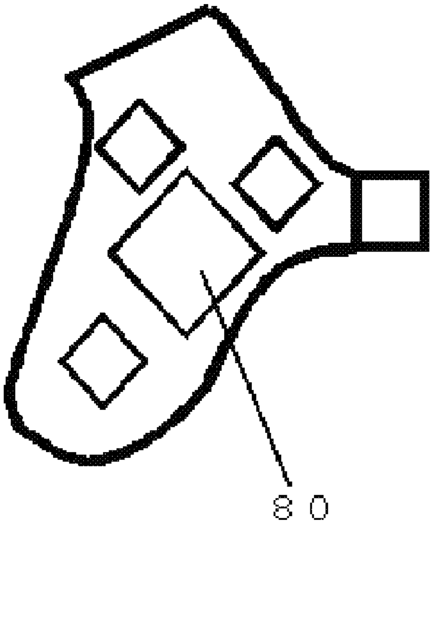

FIG. 2 are views illustrating structure of the cushion section of the neckband-type earphone according to the first embodiment of the present invention. FIG. 2(*a*) is a cross-sectional view illustrating the cushion section of a hollow type. FIG. 2(*b*) is a cross-sectional view illustrating the cushion section filled with a filling material.

The holder body 60 of each earphone driver 20 illustrated in FIG. 2(*b*) includes the cushion section 70 formed of a plurality of convex portions 80. As described above, when each earphone driver 20 is attached on the auricle of the wearer, the holder body 60 comes into contact with the head of the wearer on the back side of the auricle, and at this time, the cushion, section 70 formed on the holder body 60 comes into direct-contact with the head of the wearer.

Each convex portion 80 of the cushion section 70 is made of an elastomeric material. As illustrated in FIG. 2(*a*), a hollow portion 81 is formed inside the convex portion 80, and the inside of the convex portion 80 is filled with air. As a material for the cushion section 70, a soft material such as the elastomeric material is used, and the cushion section 70 has a hollow formed therein. Thus, when coming into contact with the wearer, the convex portion 80 of the cushion section 70 is depressed to come into contact with the head, with the result that the wearer can obtain a soft wearing feeling and a close contact feeling. Further, the cushion section 70 is made of the soft material, and hence the cushion section 70 does not inflict pain to the wearer, with the result that the wearer can wear the neckband-type earphone for a long period of time. In addition, the hollow portion is easily formed, and hence the holder body 60 itself is easily manufactured.

Further, as illustrated in. FIG. 2(*b*), a filling material 82 such as gel-like silicon may be injected into an inside of the convex portion 80 of the cushion section 70. The gel-like filling material 82 is used, and thus the convex portion 80 of the cushion section 70 keeps a deformed state in conformity to a shape of the head of the wearer, which can further enhance a wearing feeling and a close contact feeling.

FIG. 3 are views illustrating other examples of the cushion section of the neckband-type earphone according to the first embodiment of the present invention.

Various combinations may be made to the number, size, arrangement, shape, and the like of the convex portions 80 of the cushion section 70.

As illustrated in FIG. 1, the cushion section 70 may be formed of three convex portions 80. In addition, as illustrated in FIG. 3(*a*), the cushion section 70 may be formed of one convex portion 80. Furrier, as illustrated in FIG. 1 and FIG. 3(*b*), the cushion section 70 may be formed of two or more, that is, a plurality of convex portions 80. When the wearer wears the neckband-type earphone 10, the cushion section 70 including at least one convex portion 80 can provide a stable wearing feeling to the wearer without giving discomfort to the wearer, and enables the wearer to wear the neckband-type earphone 10 for a long period of time.

Further, as the convex portions 80 of the cushion section 70, as illustrated in FIG. 1, a combination of one larger convex portion 80 and smaller convex portions 80 may be adopted. Further, as illustrated in FIG. 3(*b*), a combination of convex portions 80 having the same size may be adopted. When the cushion section 70 is formed of the plurality of convex portions 80 having the same size, the plurality of convex portions 80 come into contact with the head at she same pressure, and thus the wearer can obtain a stable wearing feeling produced from contact at uniform pressure.

Further, as illustrated in FIG. 3(*c*), the convex portions 80 of the cushion section 70 may be formed of a circular convex portion 80 and polygonal (triangular, quadrangular, or other polygonal) convex portions 80. In addition, as illustrated in FIG. 3(*d*), the convex portions 80 may be formed of only polygonal (triangular, quadrangular, or other polygonal) convex portions 80. Not circular but polygonal convex portions 80 are formed, and hence a surface having sides of a polygon generates a force of suppressing movement in a direction of the surface, to thereby prevent displacement of a contact surface between the holder body 60 and the head.

Further, as illustrated in FIG. 3(*b*) and FIG. 3(*d*), the convex portions 80 of the cushion section 70 may be formed in various arrangements. The cushion section 70 may be formed by variously arranging the convex portions 80 having various shapes as appropriate depending on use of the neckband-type earphone 10.

For example, in a case of the neckband-type earphone 10 that can be used for sports and the like, the number of the convex portions 80 of the cushion section 70 is increased, and each convex portion 80 is formed into a polygonal shape. This configuration prevents slip of the neckband-type earphone 10 off the head due to vibration of the head along with exercise.

On the other hand, in a case of use of the neckband-type earphone 10 to be worn for a long period of time without severe vibration, the cushion section 70 is formed of a small number of circular convex portions 80, and thus the cushion section 70 gives little contact feeling to the head. Thus, the wearer can wear the neckband-type earphone 10 for a long period of time, and obtain a stable wearing feeling.

As described above, according to the neckband-type earphone 10 of this embodiment, due to the cushion section 70 of the holder body 60, the neckband-type earphone 10 can be securely attached on the head of the wearer together with the ear holder section 50 of each earphone driver 20, and a vicinity of each distal end portion of the neckband 30 does not tighten the head of the wearer. Thus, without feeling discomfort, the wearer can wear the neckband-type earphone 10 for a long period of time with a stable wearing feeling.

Further, the neckband-type earphone 10 does not include protruding distal end portions of the neckband 30, which may be used when the wearer puts on the neckband-type earphone. Accordingly, even a person who does not know how to use the neckband-type earphone 10 has no risk in that the distal end portions may hit the ear or the head of the person when the person puts on the neckband-type earphone 10.

In addition, the neckband-type earphone 10 does not include the protruding distal end portions of the neckband 30, which may be used when the wearer puts on the neckband-type earphone, and hence the distal end portions are not broken and damaged.

Therefore, according to the neckband-type earphone 10 of this embodiment, it is possible to provide the neckband-type earphone 10 that enables the wearer to wear the neckband-type earphone 10 for a long period of time without giving discomfort of wearing to the wearer, reduces a risk to the wearer when the wearer puts on the neckband-type earphone, and also reduces a damage-prone portion.

(Second Embodiment)

Next, a second embodiment of the present invention is described.

Figure 4:
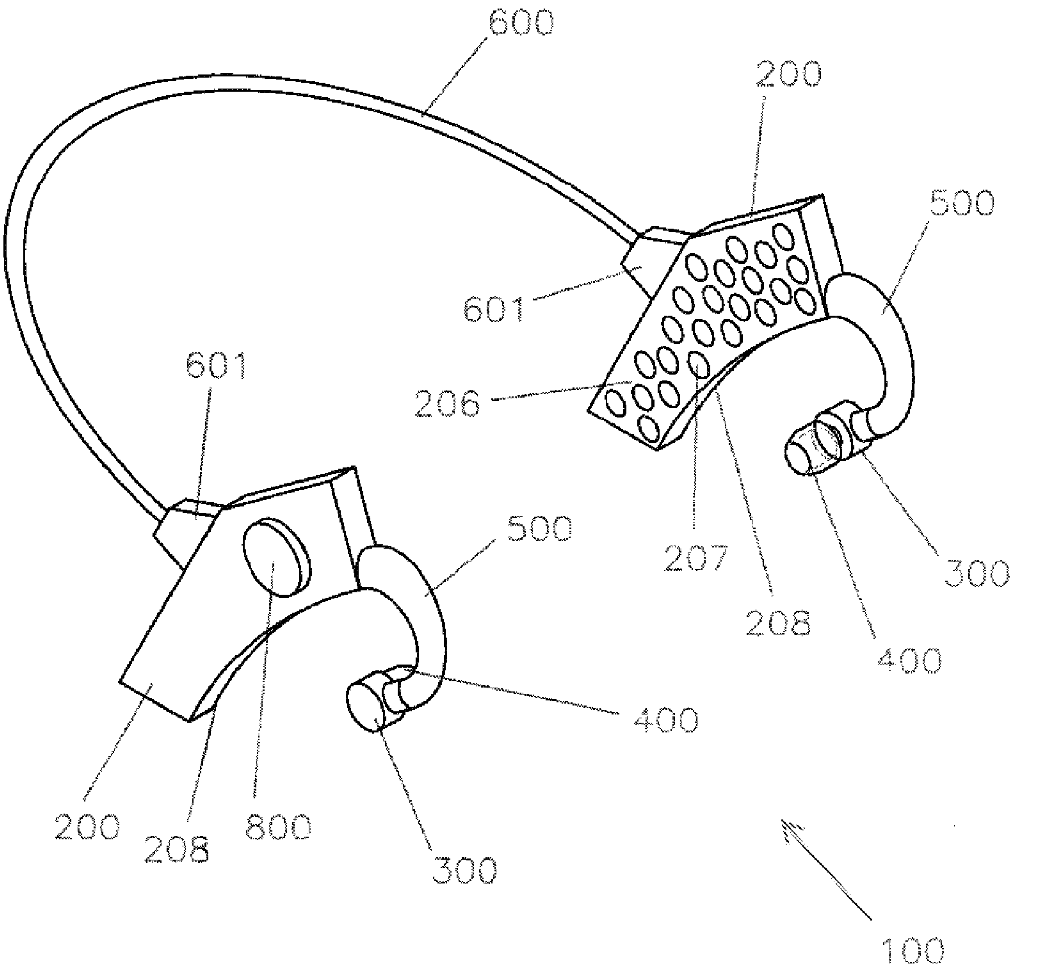
FIG. 4 is a view illustrating a schematic configuration of a neckband-type earphone according to a second embodiment of the present invention.

FIG. 4 is a view illustrating a schematic configuration of a neckband-type earphone according to the second embodiment of the present invention.

A neckband-type earphone 100 includes two head holding sections 200, two housings 300, two ear pads 400, two arm sections 500, and a neckband section 600.

The neckband section 600 is formed of an elastic body such as a curved rubber member. At each end of the neckband section 600, a connecting portion 601 for connecting the head holding section 200 is formed. The head holding section 200 is connected to the connecting portion 601. The two head holding sections 200, the housings 300, the ear pads 400, and the arm sections 500 are arranged in bilateral pairs with respect to the neckband section 600.

The head holding section 200 includes an operating section 800 on an outer surface thereof with respect to the neckband section 600. The arm section 500 is formed of an elastic body such as a rubber member, and is formed into such a curved cylindrical shape that an inside of the arm section 500 is hollow. One end of the arm section 500 is fixed to an upper surface portion of the head holding section 200, and another end of the arm section 500 is fixed to the housing 300. The housing 300 holds the ear pad 400 on an inner surface thereof with respect to the neckband section 600.

Figure 5:
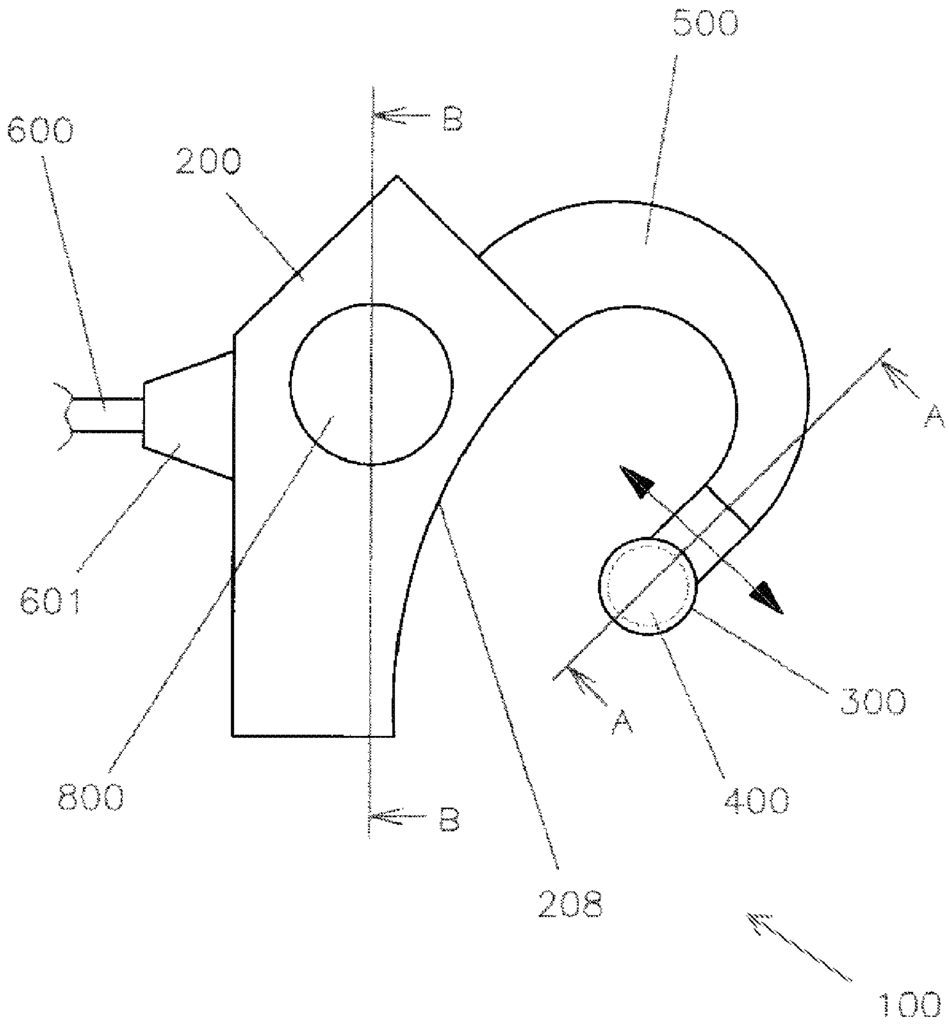
FIG. 5 is a side view illustrating a head holding section 200, an arm section 500, and a housing 300 of a neckband-type earphone 100 according to the second embodiment of the present invention.

FIG. 5 is a side view illustrating the head holding section 200, the arm section 500, and the housing 300 of the neckband-type earphone 100 according to the second embodiment of the present invention. In FIG. 5, the upper side of the drawing sheet corresponds to an upper side of the neckband-type earphone 100, and the right side of the drawing sheet corresponds to a front side of the neckband-type earphone 100.

As illustrated in FIG. 5, the arm section 500 is formed into a substantially curved semicircular shape. A curved surface portion 208 is formed on a front surface of the head holding section 200. A curved inner surface of the arm section 500 is smoothly continuous with a curved surface of the curved surface portion 208. As illustrated in FIG. 5, due to elasticity of the elastic body, the arm section 500 can be deformed in directions indicated by arrows when the housing 300 is pressed forward or backward.

Figure 6:
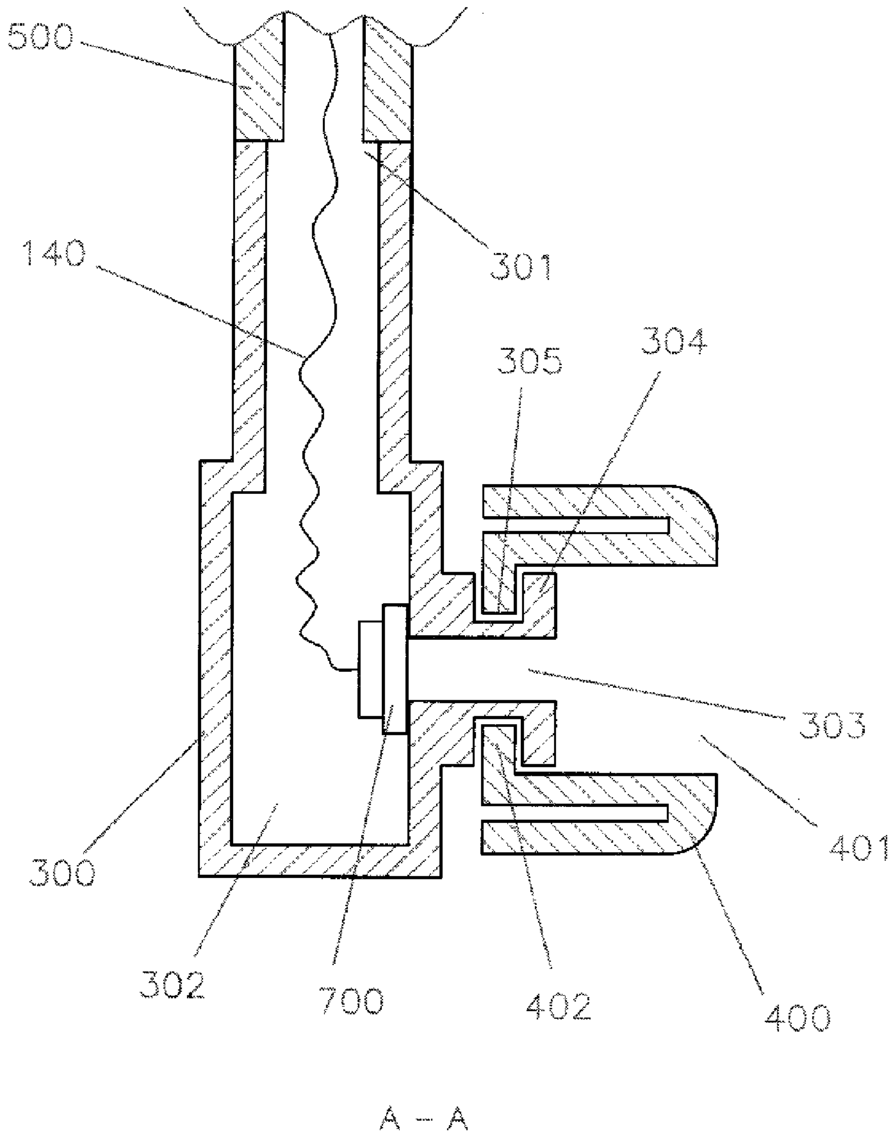
FIG. 6 is a cross-sectional view illustrating the housing 300 and an ear pad 400 of the neckband-type earphone 100 taken along the line A-A of FIG. 5.

FIG. 6 is a cross-sectional view illustrating the housing 300 and the ear pad 400 of the neckband-type earphone 100 taken along the line A-A of FIG. 5. In FIG. 6, the upper side of the drawing sheet corresponds to an upper side of the housing 300 and an upper side of the ear pad 400, and the right side of the drawing sheet corresponds to an inner side of the housing 300 and an inner side of the ear pad 400.

The housing 300 includes a driver unit 700 therein.

As illustrated in FIGS. 4 to 6, the housing 300 is formed into a cylindrical shape to include a cavity portion 302 formed therein. A hole 301 is formed in an upper side of the housing 300. The hole 301 is communicated to a cavity part formed in the arm section 500. The housing 300 includes a protruding portion 304 that forms a cylindrical shape in an inside thereof and has a hole 303 formed therein to pass through the inside of the protruding portion 304 from the cavity portion 302. A groove portion 305 is formed in a center portion of an outer periphery of the protruding portion 304.

The driver unit 700 includes a diaphragm (not shown), and is fixed to an inner wall of the housing 300 with an adhesive or the like so that the diaphragm is exposed through the hole 303 to the inner side of the neckband-type earphone. A lead wire 140 is electrically connected to the driver unit 700. The lead wire 140 is further electrically connected to an audio signal outputting unit of the head holding section 200 described below through the hole 301 via a cavity formed in the arm section 500.

The ear pad 400 is formed of an elastic body such as a rubber member and formed into a cylindrical shape. The ear pad 400 has a hole 401 formed to pass through the ear pad 400 in a fore-and-aft direction. The ear pad 400 includes a flange portion 402 protruding circumferentially inward. The ear pad 400 is held on the inner side of the housing 300 in such a manner that the flange portion 402 is fitted into the groove portion 305 of the protruding portion 304.

Figure 7:
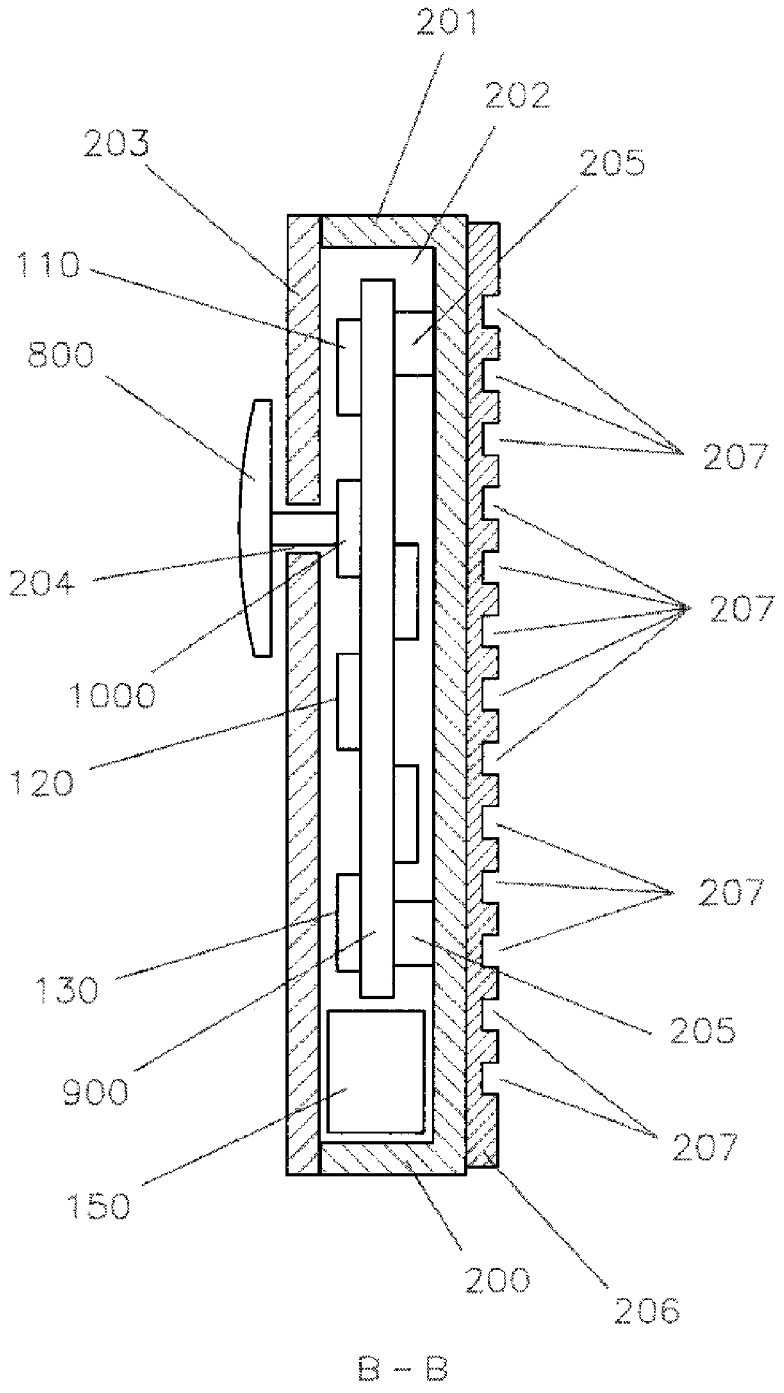
FIG. 7 is a cross-sectional view illustrating the head holding section. 200 of the neckband-type earphone 100 taken along the line B-B of FIG, 5.

FIG. 7 is a cross-sectional view illustrating the head holding section 200 of the neckband-type earphone 100 taken along the line B-B of FIG. 5. In FIG. 7, the upper side of the drawing sheet corresponds to an upper side of the head holding section 200, and the right side of the drawing sheet corresponds to an inner side of the head holding section 200.

In addition to the above-mentioned operating section 800, the head holding section 200 includes a chassis portion 201, a cover portion 203, a contact portion 206, a substrate 900, a switch 1000, an audio signal receiving unit 110, a control unit 120, an audio signal outputting unit 130, and a battery 150.

The chassis portion 201 is formed into a box-like shape that is open outward, and the chassis portion 201 includes a recessed portion 202. The cover portion 203 is formed into a plate-like shape, and is fixed so as to cover the recessed portion 202 from an outer side of the chassis portion 201. The substrate 900 is held inside the recessed portion 202 by bosses 205 fixed on the inner wall of the chassis portion 201, and the switch 1000, the audio signal receiving unit 110, the control unit 120, and the audio signal outputting unit 130 are fixed on the substrate 300. The battery 150 supplies power through the substrate 900 to the switch 1000, the audio signal receiving unit 110, the control unit 120, and the audio signal outputting unit 130. FIG. 7 illustrates the configuration in which the battery 150 is provided inside the chassis portion 201 and the cover portion 203. However, there may be adopted a configuration in which the battery 150 is removably provided on a lower surface of the chassis portion 201, or a configuration in which an open/close cover is formed as the cover portion 203 so as to allow mounting and removal of the battery 150 provided inside the chassis portion 201.

The audio signal receiving unit 110 receives an audio signal transmitted through a radio wave from a reproducing device (not shown). The operating section 800 includes a shaft on an inner side thereof, and the shaft is connected, through a hole 204 formed in the cover portion 203, to the switch 1000 fixed on the substrate 900. The operating section 800 is pressed inward, and thus the switch 1000 outputs an instruction signal for instructing start of reproduction, or stop of reproduction of the audio signal. The control unit 120 controls the audio signal receiving unit 110 and the audio signal outputting unit 130. Based on the instruction signal output from the switch 1000, the control unit 120 controls the audio signal outputting unit 130 to start or stop output of the audio signal that the audio signal receiving unit 110 has received. As described above, the audio signal outputting unit 130 is electrically connected through the lead wire 140 to the driver unit 700 provided in the housing 300. Based on control of the control unit 120, the audio signal outputting unit 130 outputs, to the driver unit 700, the audio signal that the audio signal receiving unit 110 has received.

The contact portion 206 is formed of a plate-like elastic body such as a rubber member, and is fixed on an inner side surface of the chassis portion 201. As illustrated in FIGS. 4 and 7, the contact portion 206 includes a plurality of dimple portions 207 for forming recesses in an inner surface of the contact portion 206.

When a user listens to the audio signal using the neckband-type earphone 100, first, the neckband section 600 is attached on the head of the user, and the curved surface portion 208 of each head holding section 200 is brought into abutment on a back of an earlobe. Further, under a state in which each arm section 500 is hung on an upper portion of the ear, the ear pad 400 is fitted into the ear. According to the neckband-type earphone 100, due to elasticity of the neckband section 600, backs of right and left ears of the user are sandwiched by the contact portions 206 of the head holding sections 200. Further, due to elasticity of the arm section 500, the ear is sandwiched by the ear pad 400 and the curved surface portion 208 of the head holding section 200 that is brought into abutment on the back of the earlobe. In this manner, the neckband-type earphone 100 is attached on the head and the ear of the user. Next, the reproducing device (not shown) is operated to transmit the audio signal through the radio wave from a transmitting unit of the reproducing device.

When the audio signal is transmitted through the radio wave from the transmitting unit of the reproducing device, the neckband-type earphone 100 inputs, by the audio signal receiving unit 110, the audio signal transmitted through the radio wave from the transmitting unit, of the reproducing device. When the operating section 800 is pressed by the user and the instruction signal for instructing reproduction is output from the switch 1000, the control unit 120 controls the audio signal outputting unit 130 to output the audio signal input by the audio signal receiving unit 110. Based on control of the control unit 120, the audio signal outputting unit 130 outputs the audio signal, which is input from the audio signal receiving unit 110, to the driver unit 700 through the lead wire 140. The driver unit 700 converts the audio signal input from the audio signal outputting unit 130 into vibration through use of a magnetic circuit, and the vibration is transmitted to the diaphragm through a voice coil (not shown). Thus, the audio signal is emitted as sound. In this way, the audio signal reproduced by the reproducing device is emitted as the sound by the driver unit 700 through the audio signal receiving unit 110, the audio signal outputting unit 130, and the lead wire 140, and the audio signal emitted as the sound is transmitted to an inside of the ear pad 400 through the hole 303 of the housing 300. Thus, the audio signal is transmitted to the ear of the user who wears the ear pad 400, and the user can listen to the audio signal output from the neckband-type earphone 100.

According to the neckband-type earphone 100 of this embodiment, due to elasticity of the neckband section 600, the backs of the right and left ears of the user are sandwiched by the contact portions 206 of the head holding sections 200. Further, due to elasticity of the arm section 500, the ear is sandwiched by the ear pad 400 and the curved surface portion 208 of the head holding section 200 that is brought into abutment on the back of the earlobe. Thus, the neckband-type earphone 100 can be precisely attached on the head and the ear of the user. At this time, the contact portion 206, which is brought into abutment on the back of each of the right and left ears of the user, includes the plurality of dimple portions 207 for forming recesses in the surface of the contact portion 206, and hence a surface of the head of the user on the back of the ear is gripped by the recesses of the dimple portions 207. Accordingly, even when the audio signal receiving unit 110 for receiving the audio signal transmitted from the reproducing device, the audio signal outputting unit 130, the battery 150, and the like are provided inside the head holding section 200, the dimple portions 207 of the contact portion 206 grip and hold the surface of the head of the user. Thus, for example, even when the user walks during commuting to work or plays sports such as jogging in a state of wearing the neckband-type earphone 100, the neckband-type earphone 100 can be prevented from failing off or slipping off the ear.

Further, according to the neckband-type earphone 100 of this embodiment, the battery 150 and various types of circuits for causing the driver unit 700 to receive the audio signal transmitted from the reproducing device and output the received audio signal are provided inside the head holding section 200 that is brought into abutment on the surface of the head of the user on the back of the ear. Thus, for example, even in a case where the head of the user vibrates up and down when the user walks during commuting to work or plays sports such as jogging in a state of wearing the neckband-type earphone 100, a load of a weight of the head holding section 200 is substantially equally distributed on a peripheral portion of the ear of the user by the arm sections 500 and the dimple portions 207 of the contact portions 206, and hence the neckband-type earphone 100 can be attached on the user continuously and precisely. Accordingly, for example, unlike the neckband-type earphone in which various types of circuits and the battery are provided to a back portion of the neckband section, the neckband-type earphone 100 of this embodiment can prevent a situation where the head is tilted forward or backward because of up-and-down vibration of the neckband-type earphone and thus wearing comfort of the neckband-type earphone is deteriorated.

According to the neckband-type earphone 100 of this embodiment, the operating section 800 is provided on the outer side surface of the head holding section 200, and the user presses the operating section 800 to start or stop reproduction of the audio signal. With this configuration, every time the user desires to start or stop reproduction of the audio signal and presses the operating section 800, the dimple portions 207 of the contact portions 206 are pressed on the head of the user. Accordingly, for example, even under a state in which the user wears the neckband-type earphone 100 for a long period of time, every time the user presses the operating section 800, the recesses of the dimple portions 207 can newly grip the surface of the head of the user on the back of the ear. As a result, the neckband-type earphone 100 can be attached on the head of the user reliably for a long period of time.

The neckband-type earphone 100 of this embodiment has a configuration in which the contact portion 206 including the dimple portions 207 is formed of the elastic body. However, as long as the recessed portions of the dimple portions 207 can hold the head of the user accurately, the contact portion 206 may be formed of a metal member or a plastic member other than the elastic body. Accordingly, various types of coloring and decoration can be made to the contact portion 206, and hence beauties of the neckband-type earphone 100 can be enhanced.

The neckband-type earphone 100 of this embodiment has a configuration in which the audio signal receiving unit 110 receives the audio signal transmitted from the reproducing device through the radio wave. However, the audio signal may be transmitted from the reproducing device through use of infrared communication or another data transmitting means, and the audio signal receiving unit may receive the audio signal transmitted by the transmitting means. Further, without receiving the audio signal from the reproducing device through use of wireless means such as the radio wave, the audio signal may be input through a cable or the like.

The neckband-type earphone 100 of this embodiment outputs the instruction signal for instructing start of reproduction of the audio signal or stop of reproduction of the audio signal in such a manner that the operating section 800 of the head holding section 200 is pressed. However, in addition to the instruction for start or stop of reproduction, the neckband-type earphone 100 may be capable of instructing, for example, volume adjustment of the audio signal to be output from the driver unit 700, designation of a track to be reproduced, and designation of reproduction tempo.

According to the neckband-type earphone 100 of this embodiment, a separate device other than the neckband-type earphone 100 is used as the reproducing device for reproducing the audio signal, and the neckband-type earphone 100 receives the audio signal transmitted from the reproducing device. However, for example, the neckband-type earphone 100 may have a configuration in which a storage unit for storing the audio signal and a reproducing unit are provided inside the head holding section 200 of the neckband-type earphone 100, and the reproducing unit reproduces the audio signal stored in the storage unit. With this configuration, even when a separate reproducing device is not prepared in addition to the neckband-type earphone 100, the user can listen to the audio signal using only the neckband-type earphone, and hence the user does not need to care about a connection cable and the like and can concentrate on playing sports when the user walks during commuting to work or plays sports such as jogging.

INDUSTRIAL APPLICABILITY

The present invention can be effectively used in the neckband-type earphone.

REFERENCE SIGNS LIST

10 neckband-type earphone, 20 earphone driver, 30 neckband, 40 earphone section, 50 ear holder section, 60 holder body, 70 cushion section, 80 convex portion, 81 hollow portion, 82 filling material, 100 neckband-type earphone, 200 head holding section, 201 chassis portion, 202 recessed portion, 203 cover portion, 204 hole, 205 boss, 206 contact portion, 207 dimple portion, 208 curved surface portion, 300 housing, 301 hole, 302 cavity portion, 303 hole, 304 protruding portion, 305 groove portion, 400 ear pad, 401 hole, 402 flange portion, 500 arm section, 600 neckband section, 601 connecting portion, 700 driver unit, 800 operating section, 300 substrate, 1000 switch, 110 audio signal receiving unit, 120 control unit, 130 audio signal outputting unit, 140 lead wire, 150 battery.

The invention claimed is:

1. A neckband-type earphone for outputting an audio signal, comprising:

a neckband section formed of an elastic body into a curved shape;

a driver unit fixed to a housing, the driver unit comprising a diaphragm for emitting the audio signal as sound;

a head holding section connected to the neckband section, for outputting the audio signal to the driver unit, further comprising:

a chassis portion;

a cover portion attaching to and covering a first side of the chassis portion;

a contact portion attached to a second side of the chassis portion;

a substrate disposed within the chassis portion;

a switch affixed to the substrate; and an operating section on the cover portion comprising a shaft connected through a hole in the cover portion to the switch; and an arm section formed of a curved elastic body, for connecting the head holding section and the housing together, wherein the contacting portion comprises a plurality of dimple portions for forming recesses in a side surface of the head holding section.

2. A neckband-type earphone according to claim 1, wherein each of the plurality of dimple portions is formed of an elastic body.

3. A neckband-type earphone according to claim 1, wherein the head holding section comprises:

an audio signal receiving unit for receiving the audio signal; and an audio signal outputting unit for outputting, to the driver unit, the audio signal received by the audio signal receiving unit.

4. A neckband type earphone according to claim 1, wherein the chassis portion further comprises an audio signal receiving unit.

5. A neckband-type earphone according to claim 1, wherein the chassis portion further comprises a control unit.

6. A neckband-type earphone according to claim 1, wherein the chassis portion further comprises an audio signal outputting unit.

7. A. neckband-type earphone according to claim 1, wherein the chassis portion further comprises a battery.

* * * * *